US007736366B2

(12) United States Patent
Abdelgany et al.

(10) Patent No.: US 7,736,366 B2
(45) Date of Patent: Jun. 15, 2010

(54) BONE GRAFT FORMING GUIDE

(75) Inventors: Mahmoud F. Abdelgany, Bartonsville, PA (US); Stephen Noel, Sioux City, IA (US); Alan Yeadon, Ridgewood, NJ (US)

(73) Assignee: Stryker Spine (FR)

( * ) Notice: Subject to any disclaimer, the term of this patent is extended or adjusted under 35 U.S.C. 154(b) by 977 days.

(21) Appl. No.: 10/645,235

(22) Filed: Aug. 21, 2003

(65) Prior Publication Data

US 2004/0034362 A1  Feb. 19, 2004

Related U.S. Application Data

(62) Division of application No. 09/742,923, filed on Dec. 21, 2000, now Pat. No. 6,648,894.

(51) Int. Cl.
*A61F 5/00* (2006.01)
(52) U.S. Cl. .................. 606/86 R; 600/36; 623/923
(58) Field of Classification Search ............ 606/79–80, 606/86, 87, 53, 86 R, 96–98; 83/687, 691; 249/59, 102–104, 170; 425/295, 298, 317; 623/923; 600/36
See application file for complete search history.

(56) References Cited

U.S. PATENT DOCUMENTS

| 550,767 | A | * | 12/1895 | Thielscher | .................. 408/97 |
| 729,439 | A | * | 5/1903 | Stein | ..................... 249/66.1 |
| 1,370,158 | A | * | 3/1921 | Ruttle | ........................ 83/629 |
| 1,959,615 | A | * | 5/1934 | Derrah | ....................... 100/125 |
| 3,222,723 | A | * | 12/1965 | Boggild et al. | ............. 425/410 |
| 3,552,711 | A | * | 1/1971 | DeLaney et al. | ............ 249/170 |
| 4,005,945 | A | * | 2/1977 | Gutman | .................. 408/115 B |
| 4,633,862 | A | | 1/1987 | Petersen | |
| 4,703,751 | A | * | 11/1987 | Pohl | ............................. 606/62 |
| 4,781,721 | A | | 11/1988 | Grundei | |
| 4,892,093 | A | | 1/1990 | Zarnowski et al. | |
| 5,078,719 | A | * | 1/1992 | Schreiber | ...................... 606/87 |
| 5,190,547 | A | * | 3/1993 | Barber et al. | ................. 606/79 |

(Continued)

FOREIGN PATENT DOCUMENTS

FR  2 770 766 A1  5/1999

(Continued)

OTHER PUBLICATIONS

Dupuy Motech—Keystone Graft Instruments Catalog.

(Continued)

*Primary Examiner*—Thomas C Barrett
*Assistant Examiner*—James L. Swiger
(74) *Attorney, Agent, or Firm*—Lerner, David, Littenberg, Krumholz & Mentlik, LLP

(57) ABSTRACT

A bone graft forming guide for providing a bone graft and a method of forming a bone graft. The guide includes a main body including a holder for holding a graft material and guide containing a pattern generally corresponding to the desired shaped of the bone graft. The forming guide may include a hole guide containing a plurality of hole guides arranged in a pattern generally corresponding to the desired shape of the bone graft. The forming guide may further include a cutting guide containing a pattern corresponding to the desired shape of the bone graft.

27 Claims, 8 Drawing Sheets

U.S. PATENT DOCUMENTS

| | | | |
|---|---|---|---|
| 5,246,444 A * | 9/1993 | Schreiber | 606/87 |
| 5,290,494 A | 3/1994 | Coombes et al. | |
| 5,329,846 A | 7/1994 | Bonutti | |
| 5,403,321 A | 4/1995 | Di Marco | |
| 5,415,663 A * | 5/1995 | Luckman et al. | 606/86 |
| 5,462,549 A | 10/1995 | Glock | |
| 5,514,139 A * | 5/1996 | Goldstein et al. | 606/79 |
| 5,601,563 A | 2/1997 | Burke et al. | |
| 5,624,444 A * | 4/1997 | Wixon et al. | 606/88 |
| 5,662,656 A * | 9/1997 | White | 606/88 |
| 5,749,876 A * | 5/1998 | Duvillier et al. | 606/88 |
| 5,824,084 A | 10/1998 | Muschler | |
| 5,888,219 A * | 3/1999 | Bonutti | 128/898 |
| 5,916,220 A * | 6/1999 | Masini | 606/88 |
| 6,007,537 A | 12/1999 | Burkinshaw et al. | |
| 6,033,438 A | 3/2000 | Bianchi et al. | |
| 6,096,081 A | 8/2000 | Grivas et al. | |
| 6,127,596 A | 10/2000 | Brown et al. | |
| 6,174,311 B1 | 1/2001 | Branch et al. | |
| 6,200,347 B1 | 3/2001 | Anderson et al. | |
| 6,214,368 B1 | 4/2001 | Lee et al. | |
| 6,247,914 B1 * | 6/2001 | Lindquist et al. | 425/294 |
| 6,258,095 B1 | 7/2001 | Lombardo et al. | |
| 6,293,970 B1 | 9/2001 | Wolfinbarger et al. | |
| 6,322,785 B1 | 11/2001 | Landesberg et al. | |
| 6,379,385 B1 * | 4/2002 | Kalas et al. | 623/17.11 |
| 6,383,221 B1 | 5/2002 | Scarborough et al. | |
| 6,458,158 B1 | 10/2002 | Anderson et al. | |
| 6,503,277 B2 | 1/2003 | Bonutti | |
| 6,511,509 B1 | 1/2003 | Ford et al. | |
| 6,575,980 B1 * | 6/2003 | Robie et al. | 606/88 |
| 6,676,662 B1 * | 1/2004 | Bagga et al. | 606/87 |

FOREIGN PATENT DOCUMENTS

| | | |
|---|---|---|
| WO | WO-99/09914 | 3/1999 |
| WO | WO-02/09597 A2 | 2/2002 |

OTHER PUBLICATIONS

Osteotech, Inc.—Bio D Threaded Cortical Bone Dowel Catalog.
Sulzer Medica Product Catalog.
DuPuy Acro Med—VG2 Interbody Bone Grafts Product Information Catalog Jan. 2000.
Medtronic Sofamor Danek—Tangent Posterior Discectomy and Grafting Instrumentation Set Surgical Technique Catalog 1999.
Koros Product Catalog—p. 72, "Bone Cutting Jig".
European Search Report dated Jul. 11, 2003.

* cited by examiner

BONE GRAFT FORMING GUIDE

CROSS-REFERENCE TO RELATED APPLICATIONS

The present application is a divisional of Ser. No. 09/742,923 now U.S. Pat. No. 06,648,894, filed on Dec. 21, 2000.

FIELD OF THE INVENTION

The present invention relates to bone grafts for use in the repair, replacement, and/or augmentation of various portions of animal or human skeletal systems. More particularly, the present invention relates to a prepared bone graft, guides for forming bone grafts and methods of forming bone grafts.

BACKGROUND OF THE INVENTION

Several procedures involve the use and implantation of autograft bone, allograft bone or xenograft bone into an animal or human body. At least some of the benefits of implanted bone includes providing support, promoting healing, filling bony cavities, separating or spacing bony elements such as vertebral bodies, promoting fusion, and stabilizing the site of fractures.

In one known procedure, a donor bone from a cadaver is selected and prepared for insertion into a patient. For example, a spinal implant may be prepared by selecting a femur or tibia bone and cutting the bone to a desired shape. Alternatively, a portion of a bone can be cut from the patient receiving the implant, usually from a large bone such as a hip bone. In another known procedure, the bone graft can be a synthetic material which has been formed to a desired size and shape.

Typically, bone grafts are prepared outside the operating room in a production facility, and inserts are prepared having a variety of shapes and sizes so that the physician performing a bone implant operation can select a properly sized and shaped implant for each patient and procedure. Production of bone graft can be expensive because the production facility must be capable of producing sterile implants, and the bone graft must be stored prior to use in an operation.

For many procedures, it may be desirable to provide a roughened or irregular surface on at least one surface of the finished bone graft to promote fusion of the graft to adjacent bone in the body. In addition, during an operation requiring an insert having a very precise size and shape, for example, a discectomy and spinal fusion procedure, a surgeon must have on hand a variety of bone graft sizes and shapes to precisely fit the bone graft into the disc space of the patient after preparation of the bone graft, which may include surgical removal of a ruptured or degenerated disc or a portion thereof.

Presently known methods for preparing bone grafts have shortcomings. One shortcoming is the cost of manufacturing bone grafts and sterilizing and storing the bone grafts in a production facility. Another shortcoming is the difficulty of forming a roughened or irregular surface on a bone graft, particularly after the bone graft has been cut to a desired size and shape. Formation of the roughened or irregular surface typically requires machining after cutting of the bone graft, and this may alter the dimensions or shape of the bone graft.

In view of these and other shortcomings associated with providing bone grafts, it would be desirable to provide an improved method and apparatus for the manufacture of bone grafts. Such a method should be relatively simple, inexpensive and provide the flexibility of allowing the bone graft to be prepared intraoperatively in an operating room.

SUMMARY OF INVENTION

Accordingly, the present invention generally provides a relatively simple bone graft forming guide and a method of forming a bone graft. The method includes the steps of selecting the shape of at least a portion of a bone graft and forming a plurality of holes in a graft material. According to one aspect of the invention, the plurality of holes forms a pattern generally corresponding to the intended shape of the bone graft. The invention may further include cutting at least partially through the graft material along the pattern formed by the plurality of holes.

According to one aspect of the invention, the cutting step includes cutting through at least a portion of the plurality of holes resulting in a portion of the bone graft having a roughened surface. Another aspect of the invention includes providing a drill guide containing a plurality of hole guides arranged in a pattern generally corresponding to the intended shape of the bone graft. According to this aspect of the invention, the method includes positioning the drill guide with respect to the graft material and drilling into the graft material using a least a portion of the hole guides.

In another aspect of the invention, the method may further include providing a cutting guide having a pattern corresponding the intended shape of the bone graft, positioning the cutting device with respect to the graft material, and cutting the graft material using the cutting guide. In another aspect, the drilling step includes drilling through the graft material and the cutting step includes cutting through the graft material.

According to a preferred aspect of the invention, the method is performed intraoperatively in an operating room. This aspect of the invention provides the surgeon performing a bone graft insertion procedure with the flexibility to select a properly sized and shaped bone graft in the operating room. According to prior art methods, a surgeon would have to purchase various differently sized and shaped bone grafts that are fabricated in a facility outside the operating room. For example, according to one aspect of the invention, a spinal bone graft may be formed in a generally elliptical shape with respect to the cutting direction. According to this aspect of the invention, the hole guide and the cutting guide have a pattern that is generally elliptical in shape. According to another aspect of the invention, a spinal bone graft can be produced that is generally cut in a wedge shape.

Another aspect of the invention pertains to a method of forming a bone graft from a graft material including the steps of selecting the shape of at least a portion of the bone graft, providing a graft material holder and selecting from a plurality of cutting guides, each of the cutting guides having a different cutting pattern. According to this aspect of the invention, the method further includes associating the cutting guide with the graft material holder and cutting at least a portion of the bone graft material using the cutting guide.

Another aspect of the invention involves a bone graft forming guide for providing a bone graft having a desired shape. According to this aspect of the invention, the cutting guide has a main body including a holder for holding a graft material and a cutting guide-receiving structure. This aspect of the invention also includes a cutting guide containing a pattern corresponding to the desired shape of the bone graft, and the cutting guide adapted to be detachably mounted to the main body.

According to another aspect of the invention, the forming guide includes a main body having a holder for holding a graft material and a hole guide containing a plurality of hole guides arranged in a pattern generally corresponding to the desired shape of the bone graft. The forming guide further includes a cutting guide containing a pattern corresponding to the desired shape of the bone graft.

In one aspect of the invention, the hole guide is an insert and the main body includes a guide receiving opening to receive the insert. In another aspect, the cutting guide is an insert and the main body includes an opening to receive the insert. According to this aspect of the invention, the forming guide includes a securing mechanism for removably securing one or both of the hole guide insert or the cutting guide insert in the opening.

In a preferred embodiment, the securing mechanism includes a cam member associated with the main body. Preferably, the cam member cooperates with one or both of the hole guide insert or the cutting guide insert to secure one or both of the inserts to the main body. In another aspect of the invention, the hole guide insert and the cutting guide insert include a ridge adapted to cooperate with the cam member.

According to one aspect of the invention, the main body of the bone graft forming guide includes a block adapted to receive a graft material. Preferably, the block includes two members connected by a hinge. Preferably, the main body further includes a closure means such as a clamping mechanism for clamping the two members towards each other to secure the bone within the cutting guide. Preferably, the clamping mechanism includes a threaded rod and nut assembly.

According to another aspect of the invention, the forming guide includes a handle and a shaft having a proximal end and a distal end. The proximal end of the shaft is attached to the handle, and a pair of jaws extends from the distal end of the shaft. The jaws are movable between a gripping position to grip graft material during cutting of the bone graft and a releasing position to release the implant. According to this aspect of the invention, the handle includes pair of arms connected to the pair of jaws to provide a pair of gripping members that are pivotally joined. Preferably, the pair of arms includes a locking mechanism to lock the cutting guide in a plurality of positions. According to this aspect, the cutting guides are attached to at least one of the jaws. In a preferred aspect, the hole guide and the cutting guide are removable inserts. Alternatively, the hole guide and the cutting guide may be integrally formed in at least one of the jaws.

Another aspect of the invention relates to a bone graft forming guide including a handle and a shaft having a proximal end and a distal end. The proximal end of the shaft is attached to the handle, and a pair of jaws extends from the distal end of the shaft. According to this aspect of the invention, a cutting guide is associated with the jaws, and the jaws are movable between a gripping position to grip graft material during cutting of the bone graft and a releasing position to release the implant. Preferably, the handle includes a pair of arms connected to said pair of jaws to provide a pair of gripping members, the gripping members being pivotally joined.

The present invention provides a relatively simple and inexpensive way to make bone grafts. A surgeon can select a from a variety of hole guides and cutting guides to provide various sized and shaped bone grafts for a procedure. Advantageously, the method and forming guide of the invention can be used intraoperatively in an operating room setting. By forming a plurality of holes in the graft material prior to cutting of the graft material, a roughened surface is provided on at least one surface of the bone graft. In one preferred aspect of the invention, the hole guides contain round holes, and the cutting guide is positioned such that the cutting device cuts through the approximate center of the holes to provide a roughened or ridged surface on at least one surface of the bone graft. The roughened surface promotes ease of insertion of the graft and fusion of the bone graft to an adjacent bone after insertion in the body.

Additional features and advantages of the invention will be set forth in the description which follows. It is to be understood that both the foregoing summary and the following detailed description are exemplary and are intended to provide further explanation of the invention as claimed. In the following drawings, like reference characters denote similar elements throughout the several views.

DETAILED DESCRIPTION

Figure 1:
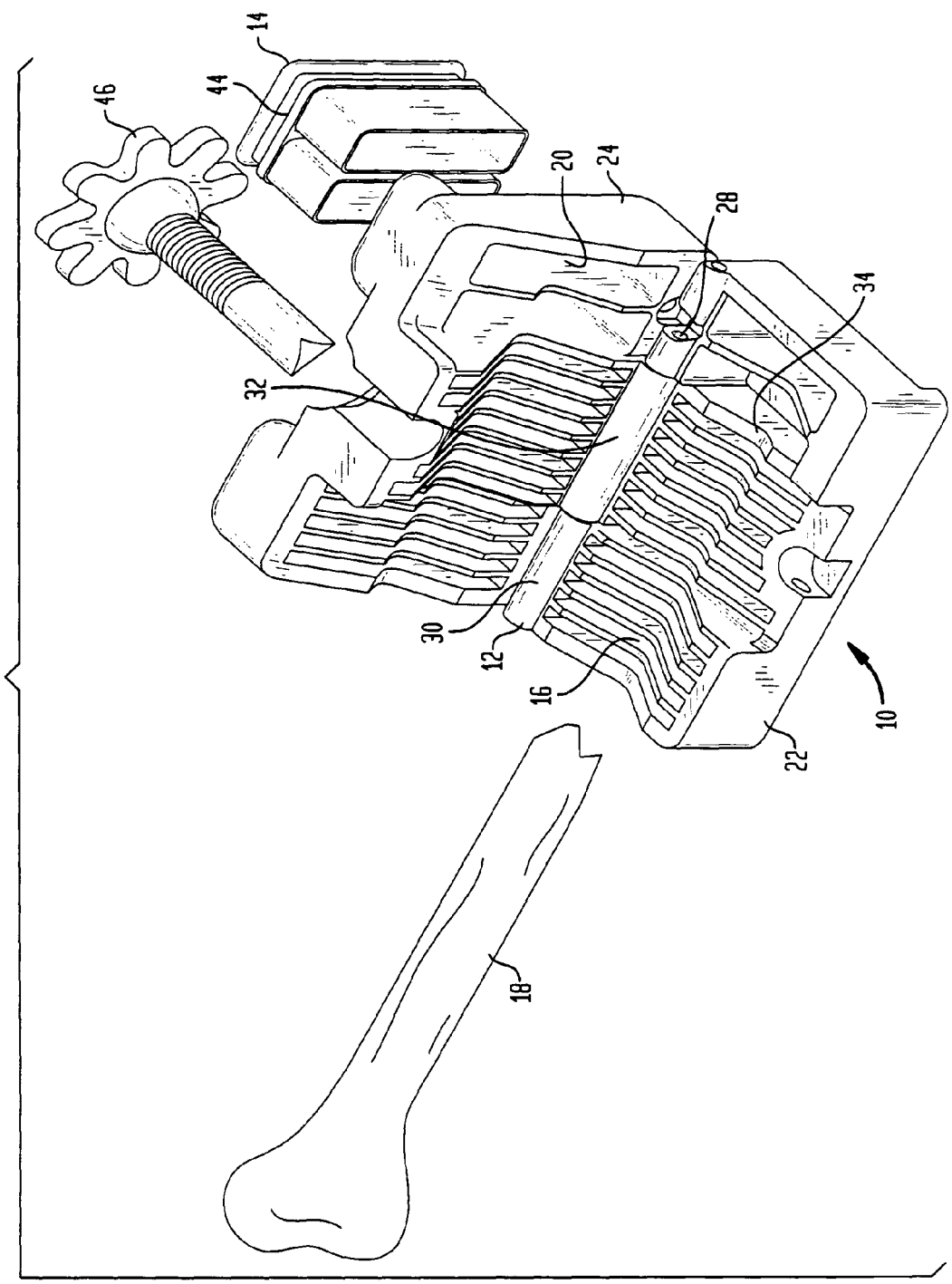
FIG. 1 is an exploded perspective view of a bone graft forming guide in an open position and a bone graft material according to one aspect of the invention.

An exemplary embodiment of the present invention is shown in FIGS. 1-7 and is designated generally by reference numeral 10. As embodied herein and referring to FIG. 1, a bone graft forming guide 10 for forming a bone graft having a desired shape includes a main body 12 and a cutting guide 14. In this embodiment, the main body is in the form of a block of material adapted to receive and, preferably, position a graft material. Preferably, the block of material comprises two members 22 and 24 connected by a hinge.

Figure 5:
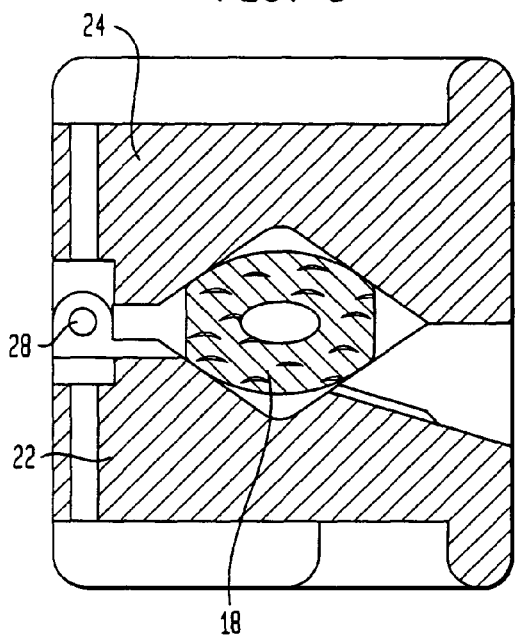
FIG. 5 is a cross-section view taken along line 5-5 of FIG. 2.

As best shown in FIGS. 1 and 5, the hinge preferably includes a pin 28, which cooperates with hinge members 30 and 32 associated with main body members 20 and 22 to join the two members together and provide an axis of rotation for opening and closing the forming guide in use. It will be appreciated, of course, that the invention is not limited by a requirement for separate body members or a requirement for a particular means of joining the members together or a specific hinge member. For example, the two members 20 and 22 may be joined together by a living hinge (not shown), wherein during the manufacturing process of the forming guide, a thinned section is provided that functions as a hinge and allows the two members to open and close. Other types of hinges are also within the scope of the invention, such as, for example, a piano hinge. Or, there may be no hinge at all, the two members being joined by any number of mechanical means.

As will be described in more detail below, the cutting guide 14 has a cutting pattern corresponding to the desired shape of the bone graft. The main body 12 of the forming guide 10 includes a holder 16 for holding bone graft material 18 during formation of the bone graft. The holder 16 may include a plurality of splines 34 on the inner surface of the main body for holding the bone graft material 18 during the forming operation. Preferably, the splines 34 are adapted to at least partially deform when they contact the graft material 18 and hold it in place during cutting of the bone graft material into a desired shape.

Figure 2:
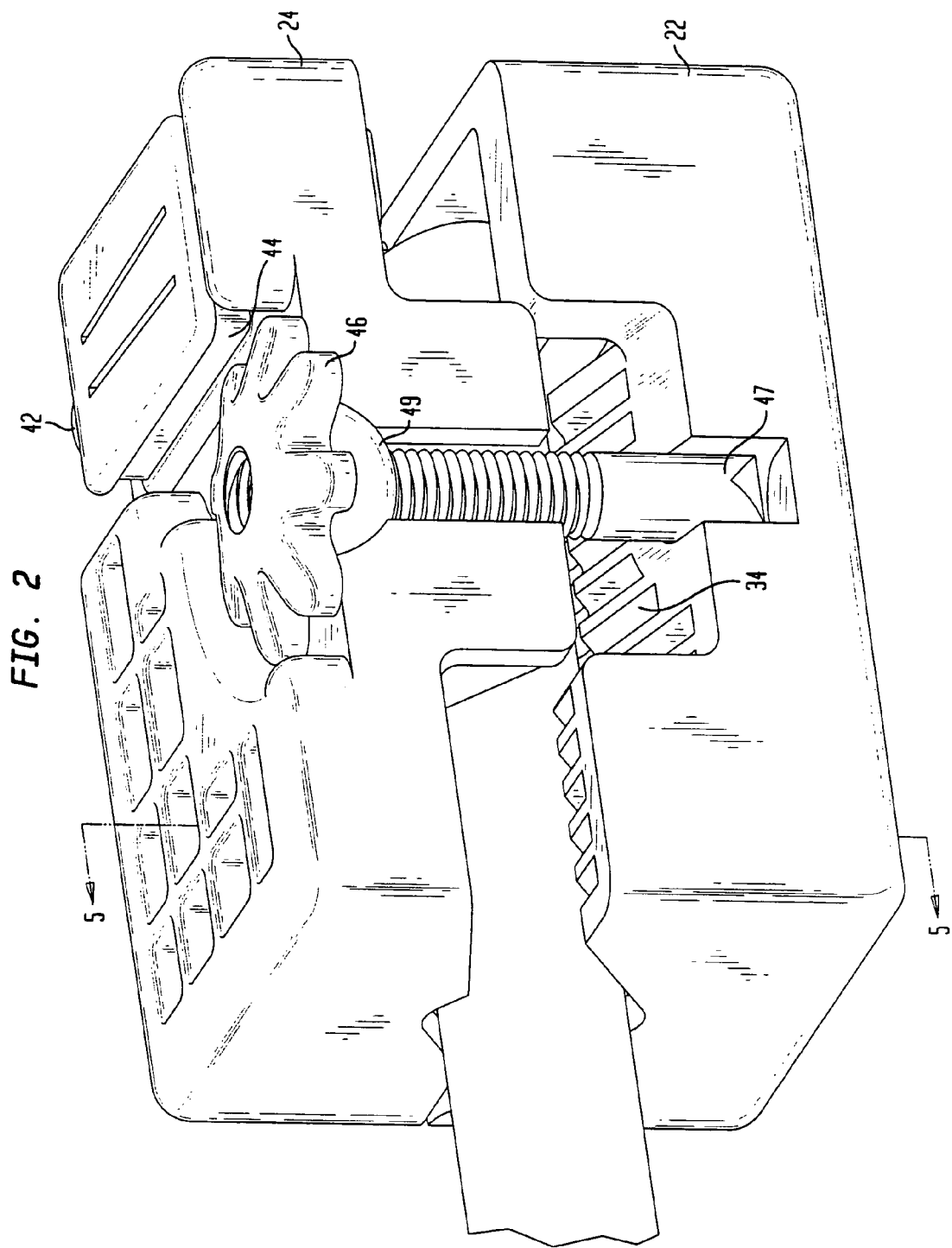
FIG. 2 is a perspective view of the forming guide of FIG. 1 in a closed position showing the bone graft material and a cutting insert in association with the forming guide.
Figure 3:
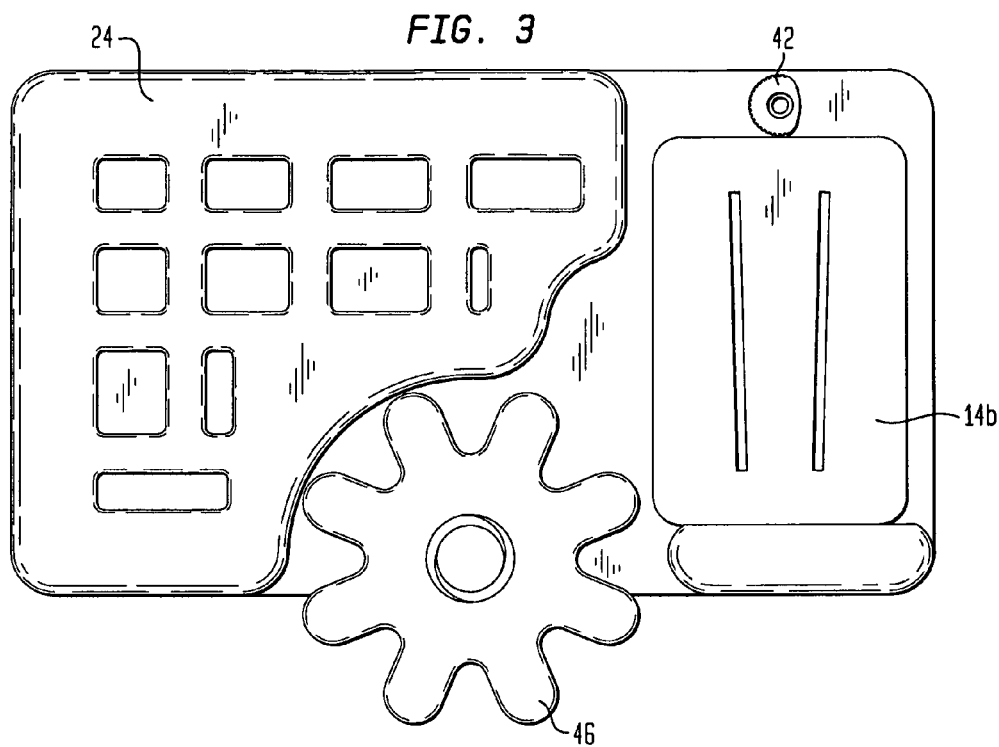
FIG. 3 is a top plan view of a forming guide according to one aspect of the invention.

According to a preferred aspect of the invention, the cutting guide 14 is adapted to be detachably mounted to the main body 12 of the forming guide. One example of various ways in which the cutting guide 14 can be detachably mounted to the main body 12 is to provide a cutting guide-receiving structure 20 associated with the main body 12, as shown in FIGS. 1-3. For example, as shown in FIG. 1, the cutting guide-receiving structure 20 may be an opening or nesting structure and the cutting guide 14 may be in the form of an insert sized to fit within the opening or nesting structure.

Figure 7A:
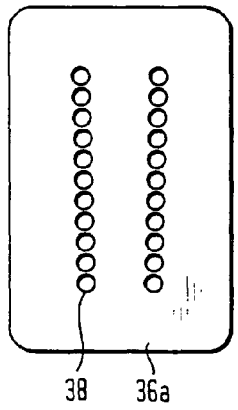
FIGS. 7A-7D show top views of examples of cutting inserts in accordance with the present invention.
Figure 7B:
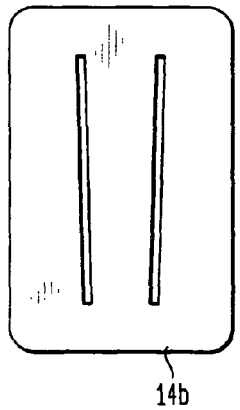
Figure 7C:
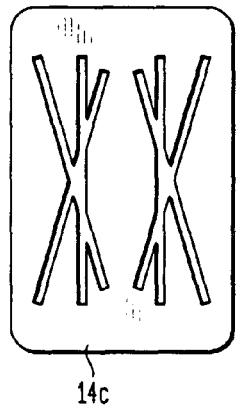
Figure 7D:
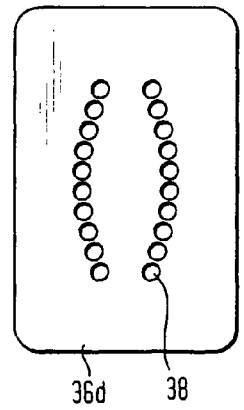

Referring now to FIG. 7A and 7C, in another aspect of the invention, the bone graft forming guide includes a hole guide 36 containing a plurality of hole guides 38 arranged in a pattern generally corresponding to the desired shape of the bone graft. According to this aspect of the invention, the hole guide 36 and the cutting guide 14 may be selected as a pair having a similarly shaped pattern for forming a bone graft. For example, hole guide insert 36a shown in FIG. 7A would desirably be used with the cutting guide insert 14b shown in FIG. 7B as described further below to provide a bone graft having a wedge shape. Similarly, the hole guide insert 36d shown in FIG. 7D would be used with the cutting guide insert 14c shown in FIG. 7C to provide an elliptically shaped bone graft, as will be described further below. It will be understood, of course, that in accordance with the present invention, a wide variety of patterns can be provided in the hole guide and cutting guide to provide various shaped bone graft. The present invention desirably provides the advantage of enabling the surgeon to custom select the size and shape of a bone graft in the operating room to fit the graft to a particular patient and/or procedure.

Thus, according to the present invention, a bone graft forming guide is provided that includes at least a main body having a holder for holding a bone graft material and a cutting guide containing a pattern corresponding to the desired shape of the bone graft. According to this aspect, the cutting guide is detachably mounted to the main body of the forming guide. In an alternative embodiment described above, the forming guide may optionally include a complementary hole guide for use with the cutting guide, the hole guide insert also adapted to be detachably mounted to the main body of the forming guide.

Figure 6:
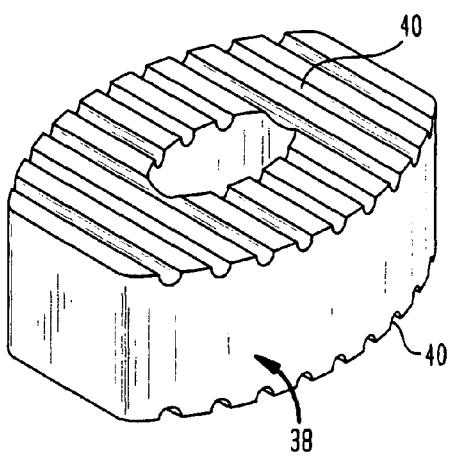
FIG. 6 is a perspective view of a bone graft in accordance with the invention.

Referring now to FIG. 6, use of a hole guide is desirable to provide a bone graft 38 having a roughened or irregular surface 40 on at least a portion of the bone graft 38. As is known in the art, it is desirable to provide a roughened surface on a portion of a bone graft to prevent the bone graft from backing out after insertion and promote fusion of the insert to adjacent tissue. For example, in a spinal fusion procedure, a ruptured disc may be replaced with a bone graft, and the portions of the bone graft contacting the adjacent vertebrae may desirably be roughened to promote fusion of the insert to the adjacent vertebrae. The present invention provides a simple and inexpensive method of forming a bone graft having a roughened surface.

According to another aspect of the invention (as shown in FIG. 3), the bone graft forming guide includes a securing mechanism 42 for removably securing one or both of the hole guide insert or the cutting guide insert in the cutting guide-receiving structure 20, which may be in the form of an opening or nesting structure adapted to receive the inserts. Preferably, the securing mechanism 42 includes a cam member associated with the main body 12 of the forming guide. The cam member 42 cooperates with one or both of the hole guide insert or the cutting guide insert 14b to secure the inserts to the main body 12. As shown in FIG. 1, the insert may optionally include a ridge 44 adapted to cooperate with the cam member to detachably secure the insert to the main body.

Figure 4:
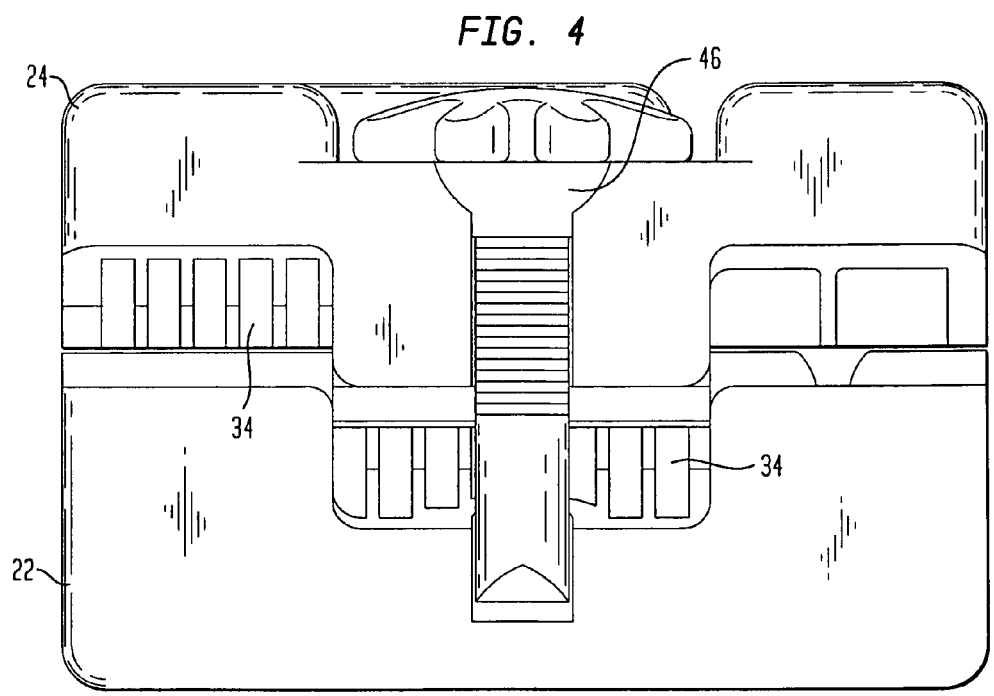
FIG. 4 is a front view of the forming guide of FIG. 2.

The forming guide preferably further includes a closure means such as a clamping mechanism 46 for moving the two members 22 and 24 towards each other to secure a bone graft material within the forming guide. As best shown in FIG. 1 and FIG. 4, the clamping mechanism 46 may include a threaded rod 47 and nut 49 assembly. A bottom portion of the threaded rod 47 may be secured to one of the members 22 in a manner to allow the threaded rod to pivot about the member 22 to move the threaded rod into and out of engagement with the other member 24. After the threaded rod is moved into engagement with the other member 24, the nut assembly 49 may be rotated until the bone graft material 18 is securely held in the holder 16 of the main body 12 (as shown in FIG. 2 and FIG. 5).

Of course, it will be understood that other closure means are within the scope of the invention. For example, the closure means can include a latch and hook assembly that is adapted to bias the two members 22 and 24 of the main body 12 together and hold bone graft material 18 in the forming guide. Alternatively, the closure means could include strap members that could be tightened to bias the two members 22 and 24 together. In addition, the closure means could be provided by screwing or bolting the main body members together, or any other suitable closure means could be used to bias the main body members together to hold the bone graft material in place during forming of the bone graft.

In use, the bone graft forming guide is preferably used intraoperatively in an operating room where a bone graft insertion procedure is performed. A surgeon would have on hand a bone graft material, for example, a donor tibia bone as shown in the Figures, or the surgeon would cut a portion of bone from the patient or obtain a synthetically formed bone graft material. The surgeon would determine the size and shape of the bone graft that was needed for the particular procedure and the patient and then cut the bone graft as follows.

According to one embodiment, the surgeon would place the bone graft material 18 in the holder 16 of the forming guide 10 and select from a plurality of cutting guides provided to the surgeon in advance. The surgeon would select the cutting guide insert that would provide the properly sized and shaped bone graft for the patient and the particular procedure. The surgeon or assistant would then associate the cutting guide with the graft material holder, preferably by inserting a cutting guide insert in the opening sized to receive the cutting guide insert. The cutting guide insert would then be secured to the main body of the forming guide by the cam member or other appropriate securing mechanism. The clamping mechanism would then be engaged to bring the two members 22 and 24 of the main body 12 together and hold the bone graft material 18 in place during cutting of the bone graft. The bone graft material would then be at least partially cut along the pattern contained in the cutting guide to provide a bone graft having a desired shape. Cutting can be performed using any appropriate cutting device known in the art, such as a sagittal saw.

If it is desirable to provide a roughened or irregular surface on at least a portion of the bone graft, the step of cutting the bone graft is preferably preceded, but may be followed, by forming a plurality of holes in a graft material, the plurality of holes forming a pattern generally corresponding to the shape of the bone graft. In the embodiments shown in FIGS. 1-7, this can easily be achieved by first inserting a hole guide insert in the insert-receiving opening in the main body, securing the insert with the securing mechanism, and then forming a plurality of holes in the bone graft material by using at least a portion of a plurality of the holes in the drill guide. As used in this disclosure, the term "drill" and "drilling" is not intended to be used in a limited manner to mean only traditional drill devices known in the art. Forming the plurality of holes may be accomplished by using a traditional drilling device and drill bits, or by other suitable machining methods such as by laser or ultrasonics.

In one embodiment, after a plurality of holes have been formed in the graft material, the hole guide insert may be removed from the opening in the main body, and a cutting guide insert may be placed in the opening. The cutting guide is then secured to the main body, and the cutting operation is performed as described above. As one example, the resulting bone graft may appear as shown in FIG. 6, having a roughened surface 40. As mentioned above, the present invention provides the flexibility of providing a wide variety of bone graft shapes, including, but not limited to, grafts that are straight, wedge-shaped, and elliptically shaped.

Figure 8:
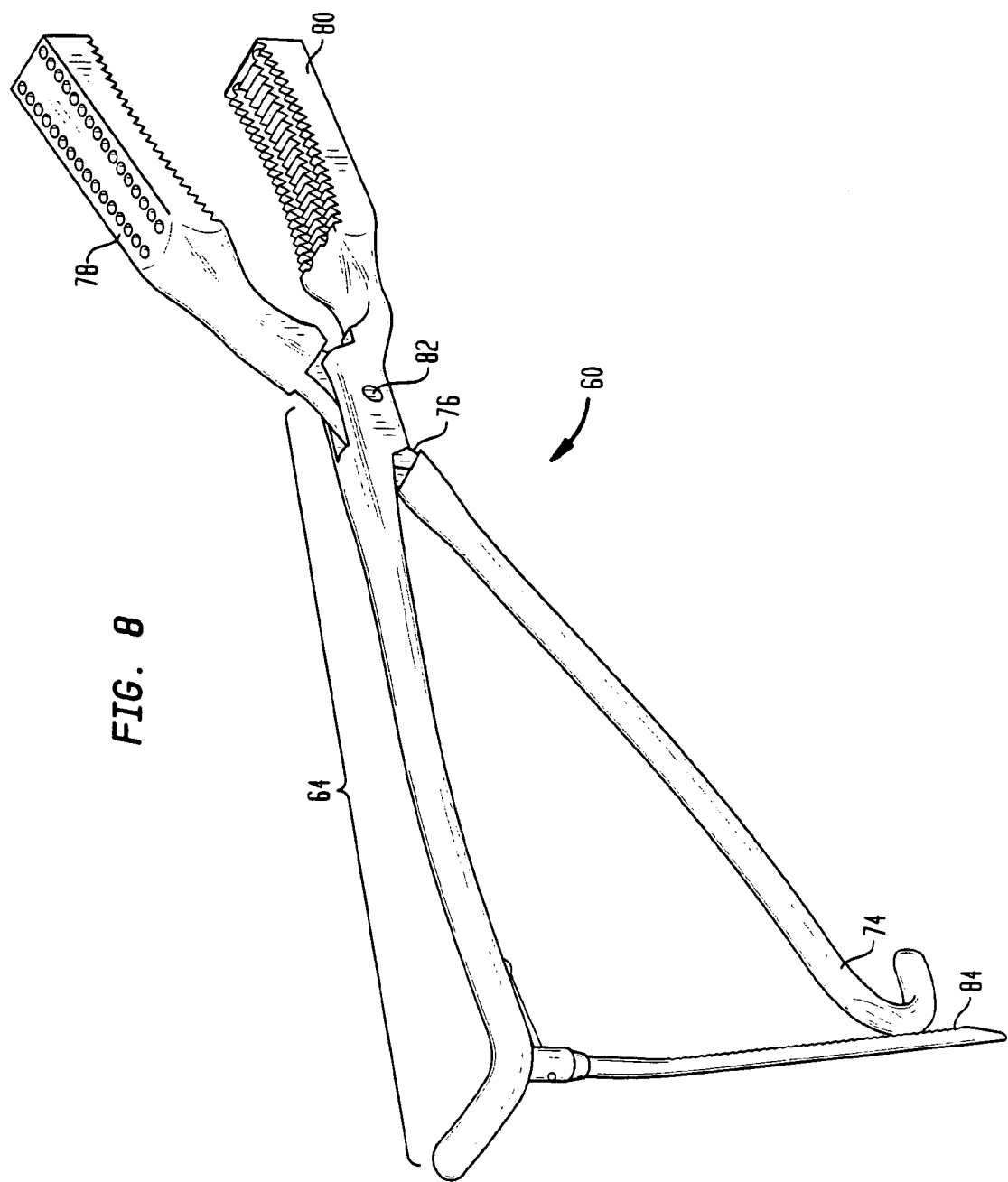
FIG. 8 is a perspective view of a bone graft forming guide according to another embodiment of the invention.

According to additional embodiments of the invention shown in FIGS. 8 and 9, the bone graft forming guide 60 has a handle 64 having a proximal end 74 and a distal end 76. According to this embodiment, a pair of jaws 78 and 80 extends from the distal end 76 of the handle 72. The jaws are movable between a gripping position to grip graft material during cutting of the bone graft and a releasing position to release the graft material (not shown). Preferably, the handle 74 includes a pair of arms connected to the pair of jaws 78 and 80 to provide the pair of gripping members, and the gripping members are pivotally joined by pivot point 82. Preferably, the pair of arms includes a locking mechanism 84 to lock the forming guide 60 in a plurality of positions. These positions could include, for example, a closed position when the jaws are locked around the bone graft material during the cutting operation.

Figure 9A:
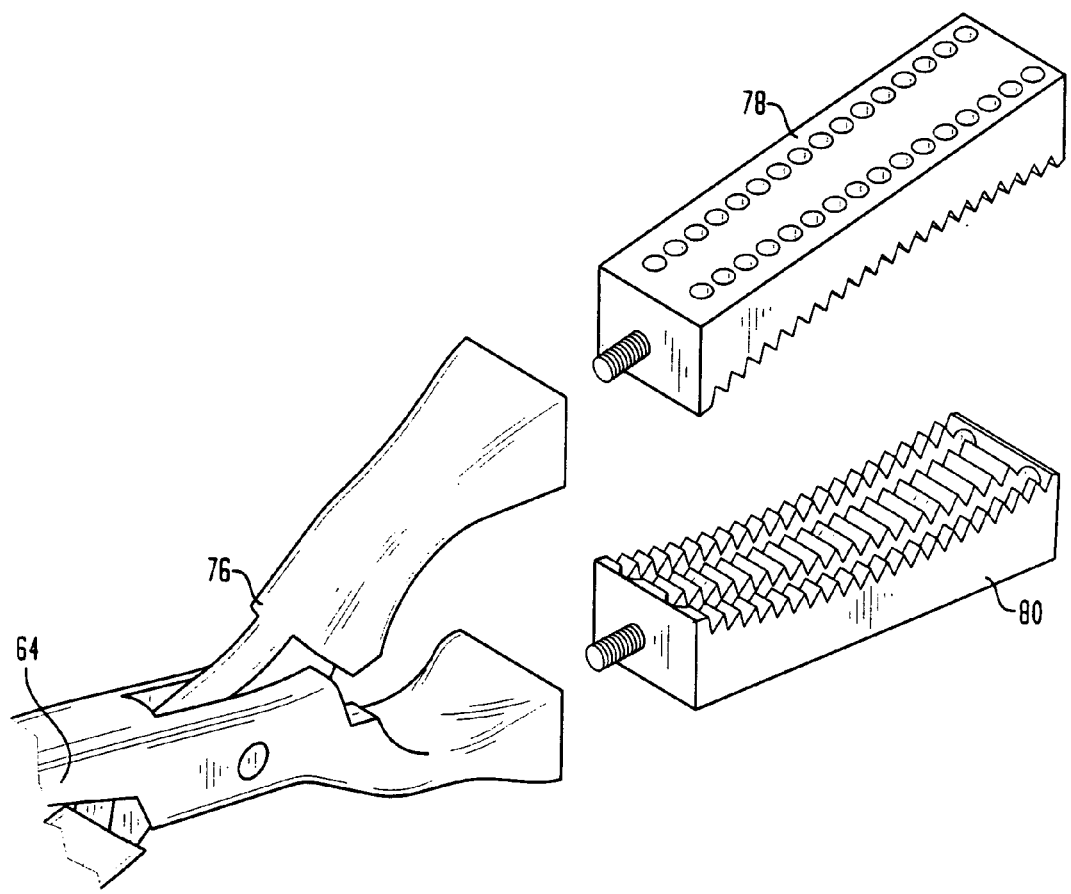
FIG. 9A-9C shows a partial perspective view of bone graft forming guides according to other embodiments of the invention.

In a preferred aspect according to this embodiment, the hole guide and/or cutting guide are attached to at least one of the jaws that make up the pair of jaws. As shown in FIG. 8, the hole guide may be integrally formed as part of the jaw. Alternatively, the hole guide and/or the cutting guide may be detachably mounted to at least one of the jaws as shown in FIG. 9a. As shown in FIG. 9A, attachment of the guides may be accomplished by screwing the guide to jaws, or by other appropriate means.

The guide may also be associated with the jaws by providing an insert receiving structure in the jaw and a hole guide insert and/or a cutting guide insert which fits into the insert similar to the insert receiving structure shown in FIGS. 1-7. Of course, if an insert structure is used, a securing mechanism may be included to secure the insert in to the jaw. Such securing mechanisms can include a cam mechanism, a ball and spring detent structure, snap, clips, or any other mechanism for securing the inserts in the insert receiving structure during cutting and forming of the bone graft.

Figure 9B:
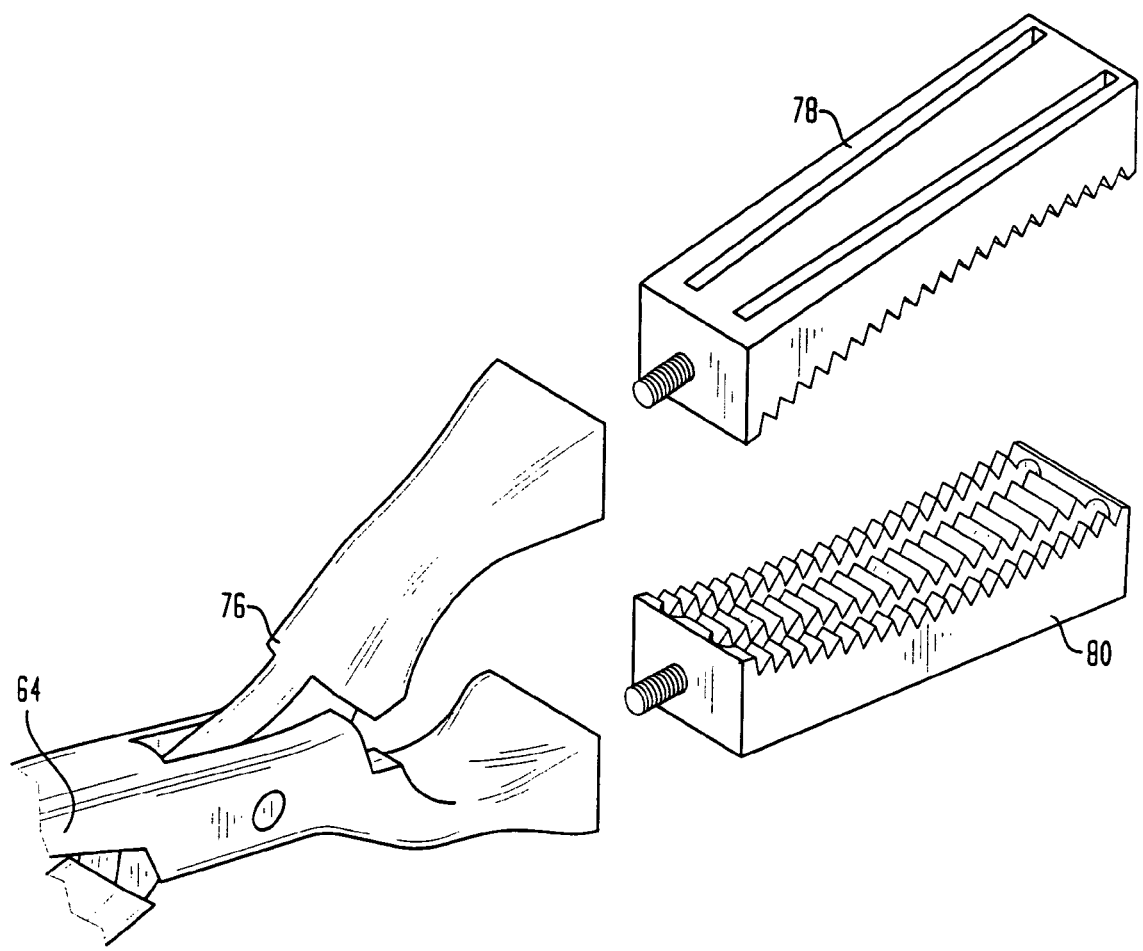
Figure 9C:
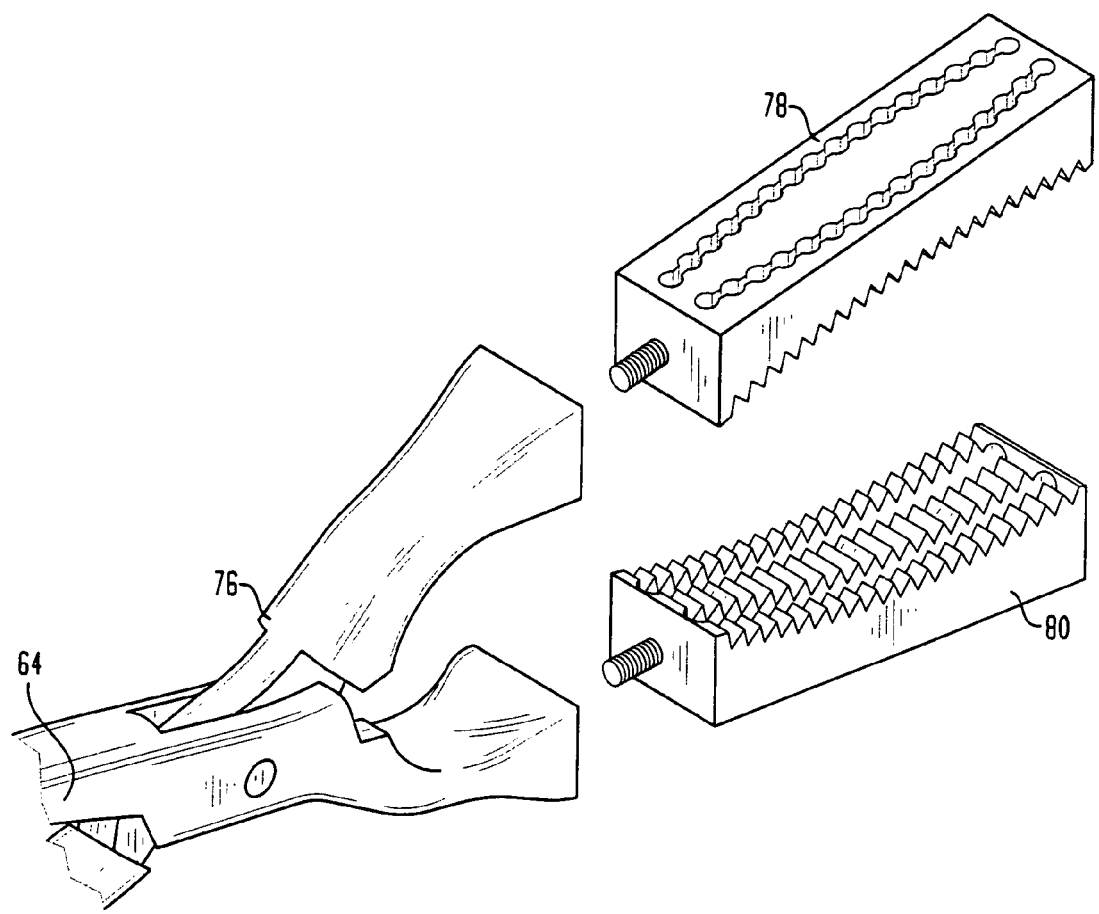

As shown in FIGS., 9b and 9c, the inserts may be provided in a variety of shapes and sizes. FIG. 9b shows a cutting guide insert for making a wedge-shape. FIG. 9c shows a combination hole-guide and cutting guide insert having a pattern of hole guides and cutting guides generally in the shape of an ellipse to form a elliptically-shaped bone graft.

In use, the embodiments shown in FIGS. 8 and 9 can be used intraoperatively in an operating room setting. Desirably, the surgeon can be provided with several forming guides having a variety of sized and shaped hole and cutting guides. The surgeon would determine the proper size and shape of the bone graft needed for the procedure. A bone graft material, such as a donor bone, would be gripped between the jaws of the forming guide, and the surgeon or assistant would apply pressure to the handles so that the jaws close on the bone graft material. The securing mechanism would lock the jaws in place, and the bone graft material could be cut to the desired shape using an appropriate cutting device such as a sagittal saw.

If it is desired to provide a bone graft implant having a roughened surface, forming holes in the graft material using at least a portion of the holes in a hole guide would precede the step of cutting the bone graft material. If the forming guide includes a combination hole guide/cutting guide in the jaw as shown in FIG. 9c, the bone could be drilled and cut using the same forming guide without having to release the bone graft material from the forming guide between the drilling and cutting steps. However, if the forming guide does not include a combination drill guide/cutting guide separate forming guides (one including a drill guide, the other including a cutting) would be utilized. Alternatively, a forming guide having detachable inserts could be used and the drill guides would be detached from the jaws after the drilling step and the cutting guides would be attached to the jaws prior to the cutting step.

The material for making the forming guide according to the present invention can be any material having the proper rigidity and strength for holding the bone graft material during the cutting and forming operations. Accordingly, plastic, metals, ceramics, composite materials, and combinations thereof can be utilized to form the various parts of the forming guide. If it is desired to reuse the forming guide, the materials used to construct the forming guide should be designed to withstand sterilization procedures.

It will be apparent to those skilled in the art that various modifications and variations can be made in the forming guide and the method of the present invention without departing from the spirit or scope of the invention. Thus, it is intended that the present invention cover the modifications and variations of this invention provided they come within the scope of the appended claims and their equivalents.

What is claimed is:

1. A bone graft forming guide for providing a bone graft having a desired shape comprising:
    a main body including first and second portions defining an interior for holding a graft material;
    a hole insert guide containing a plurality of holes arranged in a hole pattern generally corresponding to the desired shape of the bone graft, the hole pattern allowing for holes to be made along first and second spaced apart portions of the perimeter of the bone graft while the graft material is disposed within the interior; and
    a cutting guide containing a cutting pattern corresponding to the desired shape of the bone graft, the cutting pattern allowing for cuts along at least first and second spaced apart portions of the perimeter of the bone graft while the graft material is disposed within the interior,
    wherein the main body includes a guide receiving opening for the insert.

2. The bone graft forming guide of claim 1, wherein the cutting guide is an insert and the main body includes a guide receiving opening for the insert.

3. The bone graft forming guide of claim 1, wherein said cutting guide is detachably mounted to said main body.

4. The bone graft forming guide of claim 3, wherein said cutting pattern of said cutting guide comprises a plurality of bores.

5. The bone graft forming guide of claim 4, wherein said plurality of bores are interconnected.

6. The bone graft forming guide of claim 3, wherein said cutting pattern of said cutting guide comprises at least one slot.

7. The bone graft forming guide of claim 3, wherein said main body further comprises a mounting structure to facilitate detachably mounting said cutting guide to said main body.

8. The bone graft forming guide of claim 7, wherein said main body further comprises a securing element to secure said cutting guide to said mounting structure.

9. The bone graft forming guide of claim 1, wherein said first and second portions are hinged together, and wherein each have bone graft material contacting surfaces, and wherein at least one of said bone graft material contacting surfaces is deformable to facilitate holding said bone graft material when said bone graft material is clamped between said first and second hinged portions of said main body of said instrument.

10. The bone graft forming guide of claim 9, wherein said at least one of said bone graft material contacting surfaces has protrusions.

11. The bone graft forming guide of claim 9, wherein said at least one of said bone graft material contacting surfaces is non-linearly configured to accommodate a cross-sectional shape of said bone graft material.

12. The bone graft forming guide of claim 1, wherein said first and second portions each have bone graft material contacting surfaces, and wherein at least one of said bone graft material contacting surfaces is non-linearly configured to accommodate a cross-sectional shape of said bone graft material.

13. The bone graft forming guide of claim 1, wherein said pattern of said cutting guide comprises a plurality of bores.

14. The bone graft forming guide of claim 13, wherein said plurality of bores are interconnected.

15. The bone graft forming guide of claim 1, wherein said pattern of said cutting guide comprises at least one slot.

16. The bone graft forming guide of claim 1, wherein the first and second portions have respective ends pivotally connected together.

17. A bone graft forming guide for providing a bone graft having a desired shape comprising:
   a main body including a holder for holding a bone graft material, the main body including a first portion and a second portion, at least one end of the two portions being joined together to provide a holder for holding a graft material during cutting, the main body having a receiving structure adapted to receive an insert;
   a hole guide insert associated with the main body, the hole guide insert containing a plurality of holes, the plurality of holes forming a hole pattern generally corresponding to the desired shape of the bone graft, the hole pattern allowing for holes to be made along first and second spaced apart portions of the perimeter of the bone graft; and
   a cutting guide insert associated with the main body, the cutting guide insert containing a cutting pattern corresponding to the desired shape of the bone graft, the cutting pattern allowing for cuts along at least first and second spaced apart portions of the perimeter of the bone graft;
   wherein said hole guide insert and said cutting guide insert are interchangeable.

18. The bone graft forming guide of claim 17, wherein the hole guide insert and the cutting guide insert are removably insertable within the receiving structure.

19. The bone graft forming guide of claim 18, further including closure means for closing the two portions of the main body together to hold a bone graft material during forming of the bone graft.

20. The bone graft forming guide of claim 19, wherein said receiving structure further includes a cam member.

21. The bone graft forming guide of claim 17, wherein said receiving structure is an opening in said main body, said opening sized to fit only one of said hole guide insert or said cutting guide insert at any given time.

22. The bone graft forming guide of claim 17, wherein only the hole guide insert or only the cutting guide insert can be associated with the main body at one time.

23. The bone graft of claim 17, wherein the first and second portions have respective ends pivotally connected together.

24. A bone graft forming guide for providing a bone graft having a desired shape comprising:
   a main body including a holder for holding a bone graft material, the main body including a first portion and a second portion, at least one end of the two portions being joined together to provide a holder for holding a graft material during cutting, the main body having a receiving structure adapted to receive an insert;
   a hole guide insert associated with the main body, the hole guide insert containing a plurality of holes, the plurality of holes forming a hole pattern generally corresponding to the desired shape of the bone graft, the hole pattern allowing for holes to be made along first and second spaced apart portions of the perimeter of the bone graft;
   a cutting guide insert associated with the main body, the cutting guide insert containing a cutting pattern corresponding to the desired shape of the bone graft, the cutting pattern allowing for cuts along at least first and second spaced apart portions of the perimeter of the bone graft; and
   closure means for closing the two portions of the main body together to hold a bone graft material during forming of the bone graft;
   wherein the hole guide insert and the cutting guide insert are removably insertable within the receiving structure.

25. An instrument for use in forming a bone graft from bone graft material, said instrument comprising:
   a body including first and second portions, each of said first and second portions having bone graft material contacting surfaces, said first and second portions being hinged together and defining an interior capable of holding said bone graft material;
   a pattern guide associated with said body, wherein said pattern guide facilitates forming a pattern in said bone graft material corresponding to a desired shape of said bone graft, the pattern allowing for holes to be made along first and second spaced apart portions of the perimeter of the bone graft while the graft material is disposed within the interior; and
   a cutting guide associated with said body, wherein said cutting guide facilitates cutting through said pattern in said bone graft material to form said desired shape of said bone graft while the graft material is disposed within the interior;

wherein at least one of said bone graft material contacting surfaces is deformable to facilitate holding said bone graft material when said bone graft material is clamped between said two hinged portions of said body of said instrument.

26. The instrument of claim 25, wherein said at least one of said bone graft material contacting surfaces has protrusions.

27. The instrument of claim 25, wherein said at least one of said bone graft material contacting surfaces is non-linearly configured to accommodate a cross-sectional shape of said bone graft material.

* * * * *